United States Patent [19]
Renger

[11] Patent Number: 5,496,352
[45] Date of Patent: Mar. 5, 1996

[54] ACTIVITY SENSORS FOR IMPLANTABLE MEDICAL DEVICES

[75] Inventor: Herman L. Renger, Calabasas, Calif.

[73] Assignee: Pacesetter, Inc., Sylmar, Calif.

[21] Appl. No.: 223,079

[22] Filed: Apr. 4, 1994

[51] Int. Cl.[6] .......................... G01P 15/09; H01L 41/04
[52] U.S. Cl. ................................. 607/19; 128/642
[58] Field of Search .................. 128/642, 687, 128/690, 714, 716, 721, 722, 782; 607/19, 20

[56] References Cited

U.S. PATENT DOCUMENTS 5,220,836  6/1993  Harms et al. .

Primary Examiner—William E. Kamm
Assistant Examiner—Marianne Parker
Attorney, Agent, or Firm—Lisa P. Weinberg

[57] ABSTRACT

An implantable medical device including a piezoelectric accelerometer activity sensor. The activity sensor includes a thin film piezoelectric cell within a frame structure. A mass imposes a load based upon acceleration to apply lateral or transverse forces which cause the generation of an electrical potential within the piezoelectric cell, which can be used by a rate control algorithm within the device to control operation of the device.

13 Claims, 3 Drawing Sheets

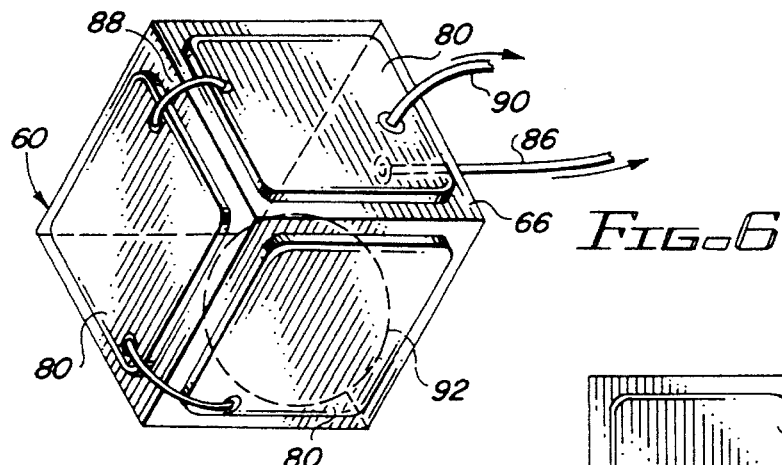
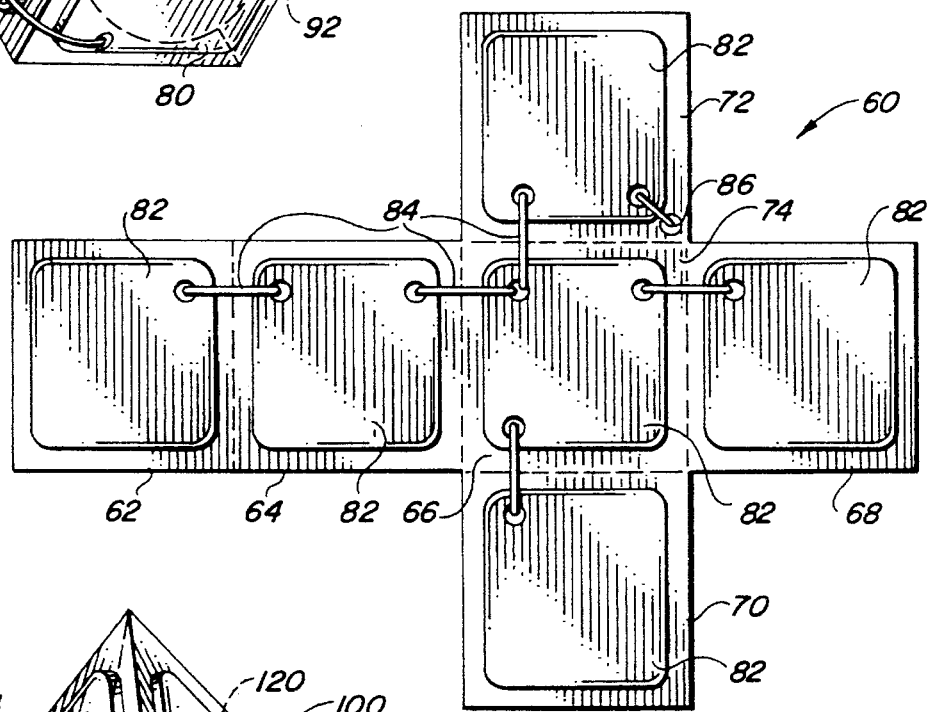
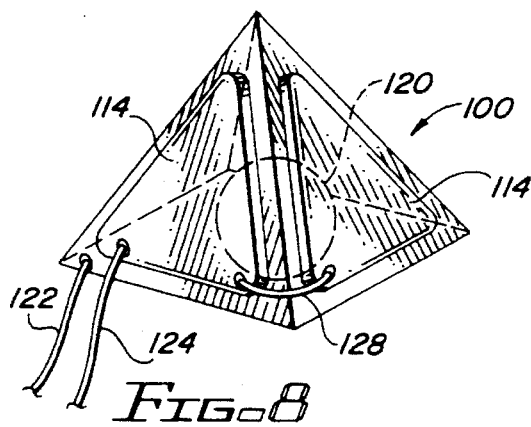
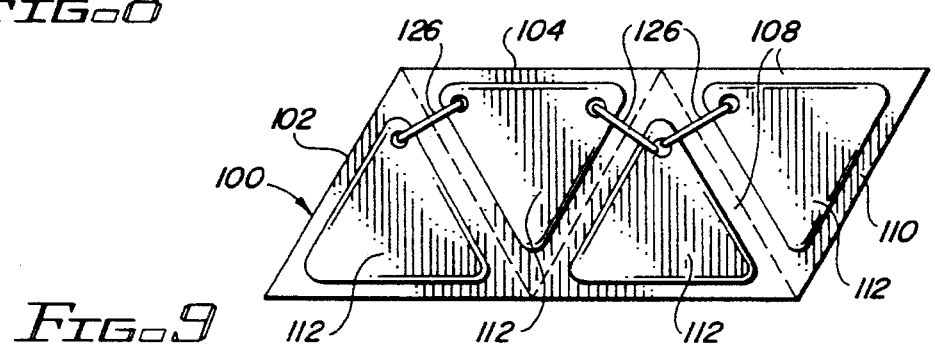

ACTIVITY SENSORS FOR IMPLANTABLE MEDICAL DEVICES

FIELD OF THE INVENTION

The present invention is directed to activity sensors for use in implanted medical devices such as cardiac pacemakers and drug pumps. More particularly, the invention is directed to an accelerometer using a piezoelectric material assembled with a mass element to be responsive to motion and acceleration, for producing an output signal useful in modifying the performance of the implanted medical device.

BACKGROUND OF THE INVENTION

There are a number of different reasons why pacemakers are implanted. Pacemakers may monitor and function only to back up the normal sinus rhythm of the heart. Alternatively, a pacemaker may provide complete control of the pacing of the heart. Rate modulated pacemakers have been developed to help patients adapt to physiological stress by increasing their heart rate. Rate modulated pacing is particularly advantageous for patients with chronic atrial defibrillation or sick sinus syndrome which prevents normal physiological sinus node response to exercise or stressful activities.

Rate modulated pacing is accomplished by providing a sensor capability, either built into the pacemaker or attached as an additional lead, in combination with a pacing rate control algorithm in the pacemaker control memory. One type of sensor presently in use is a motion detector built into the pacemaker. There are currently two types of motion detectors mounted within the pacemaker. The first is a piezoelectric material which is formed in a flat sheet and placed inside the pacemaker housing. Changes in body movement and muscle motion cause deformation of the piezoelectric crystal which produces an output signal. The output signal is dependent upon the amount of motion and can be used as a direct input into the pacing rate control algorithm.

The presently available motion detector devices are capable of providing activity responsive output signals. However, the elimination of false signals, which may result from externally imposed accelerations and motion as compared to the physical activity of the patient, remains a serious problem. For this reason, lead mounted sensors to indirectly measure physical activity have been designed which include sensors affixed to leads extending into the atrium or ventricle, which monitor temperature, blood perfusion, or respiratory rate. However, use of these types of lead-mounted sensors for the rate modulated pacemakers result in the necessity of having an additional implanted lead, and the associated problems and limitations thereof.

Accordingly, it would be beneficial to have an improved accelerometer device mounted within the pacemaker housing to provide an accurate signal indicative of physiological induced stress based on acceleration and motion of the individual, while eliminating or reducing externally imposed false signals.

BRIEF DESCRIPTION OF THE INVENTION

The present invention contemplates an implantable medical device such as a pacemaker including a piezoelectric accelerometer activity sensor mounted within the pacemaker housing. In a first embodiment, the piezoelectric accelerometer activity sensor includes a thin film of piezoelectric material extending within a frame structure. The thin film supports a mass which may be either affixed directly to the film, or spaced from a surface of the film by a cantilever element. The mass imposes a load based upon lateral or transverse motion or rotation and the resulting accelerations, which cause the generation of an electrical potential within the piezoelectric film. The piezoelectric film has conductive metallic layers or coatings on opposite faces to provide an electrical signal output, which can be used by a rate control algorithm within the pacemaker software to control cardiac activity.

An alternative design of the accelerometer contemplates forming an enclosed geometric shape, such as a cube or tetrahedron, of piezoelectric material, and placing a mass element within the enclosed geometric shape. The inertial force of the mass element against the internal surfaces of the enclosed geometric shape produces electrical output signals which can be used by the rate control algorithm. For the preferred configurations, the size and orientation of the accelerometer device and its associated mass is designed to maximize the output signal resulting from physiological motion or acceleration of the individual, and minimize the externally imposed false output signals. The signal processing techniques required to process the signals from piezoelectric elements are known and may be adapted for use with the present invention, as for example the signal processing techniques detailed in U.S. Pat. No. 5,220,836, herein incorporated by reference.

BRIEF DESCRIPTION OF THE FIGURES

FIG. 6 depicts a cube shaped activity sensor including an enclosed mass;

FIG. 7 depicts the unassembled cube-shaped activity sensor of FIG. 6, with the sides of the cube laid into a flat plane;

FIG. 8 depicts a tetrahedron shaped activity sensor enclosing a mass;

FIG. 9 depicts the tetrahedron shaped activity sensor of FIG. 8 laid into a flat plane.

DETAILED DESCRIPTION OF THE PREFERRED EMBODIMENT

Figure 1:
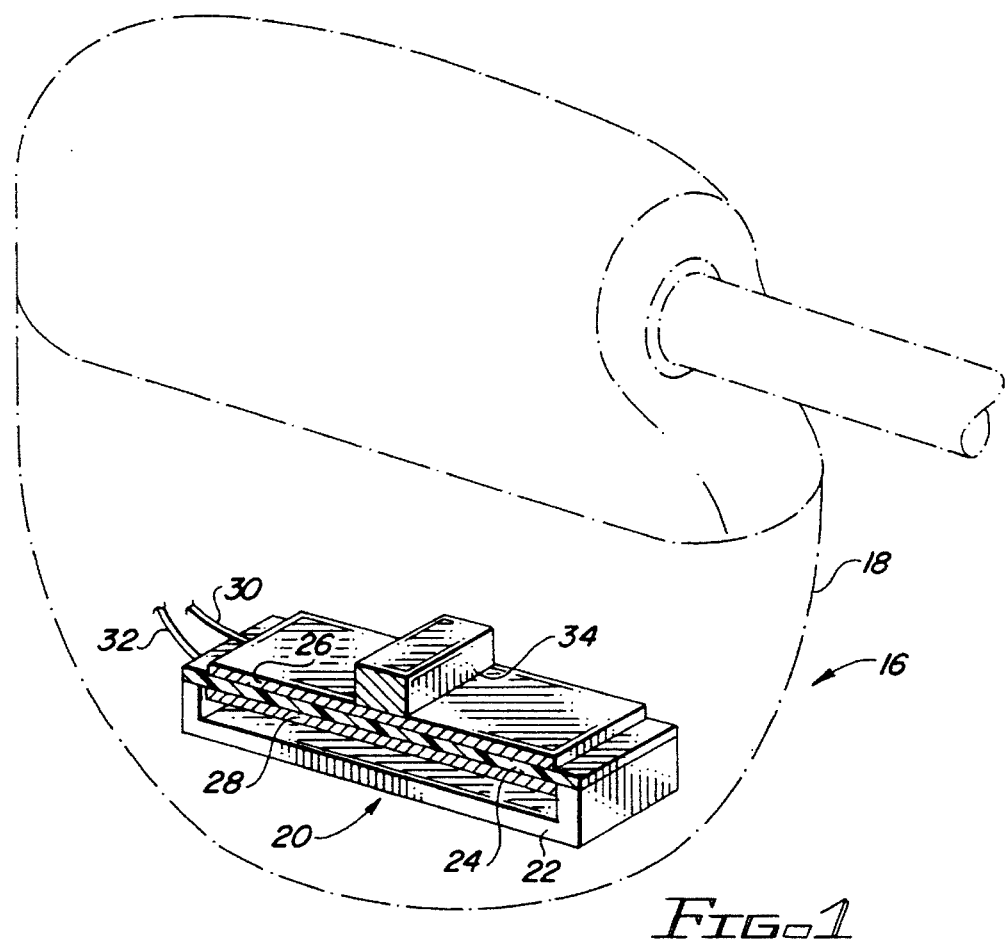
FIG. 1 is a perspective and enlarged view of a basic activity sensor placed within a pacemaker housing shown in phantom.

FIG. 1 depicts in phantom a pacemaker 16 having a housing 18. A basic activity sensor 20 according to the present invention is illustrated as being mounted within the housing 18. The relative size of the activity sensor 20 illustrated in FIG. 1 is greatly exaggerated as compared to the size of the pacemaker 16, in order to more clearly illustrate the features of the activity sensor 20.

The activity sensor 20 includes a frame assembly supporting the ends of a thin film 24. The thin film 24 is formed from a piezoelectric material such as polyvinylidene fluoride (PVDF), having a metallized coating 26, 28 on opposite major surfaces. Piezoelectric materials are characterized by the physical property of producing an electrical potential on opposite sides of a crystalline structure when subjected to stress or strain forces. When the opposing surfaces of the piezoelectric crystal are coated with conductive layers, the electrical potential in the crystal produces a voltage potential between the conductive layers proportional to the strain in the piezoelectric material. Thus, in the activity sensor 20 of FIG. 1, application of an acceleration force results in a voltage potential output as a signal on conductors 30 and 32, which are attached to the metallized coatings 26 and 28, respectively.

Affixed to one surface of the piezoelectric film 24 is a mass 34. The mass 34 has a center of gravity which is spaced from the plane of one of the major surfaces of the piezoelectric film 24. The application of inertially and/or gravitationally generated forces which are imposed on the mass 34 will cause acceleration of the mass 34, which produces an increased stress in the piezoelectric film 24. The stress in the piezoelectric film 24 will generate a voltage potential as discussed above. An output signal is routed via conductors 30 and 32 to signal processing circuitry (not shown) within the pacemaker 16, as discussed below.

Figure 2:
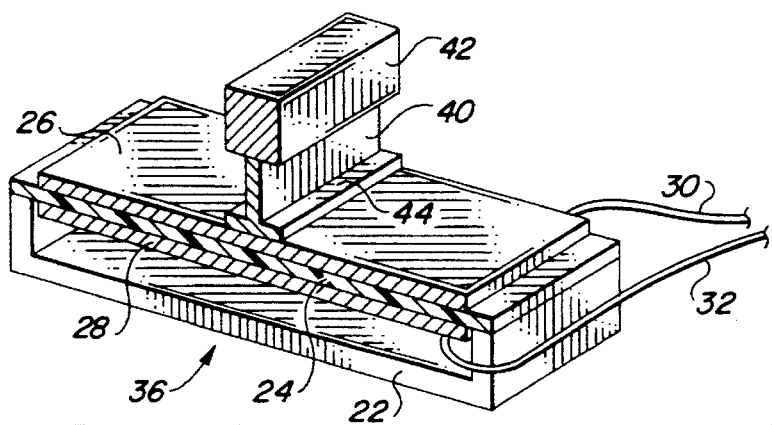
FIG. 2 is a perspective view of a first alternative version of the activity sensor of FIG. 1.

The design of the activity sensor 20 of FIG. 1 is enhanced in a first alternative embodiment shown in FIG. 2. In the first alternative embodiment an activity sensor 36 includes a number of elements common to the elements of FIG. 1, and like numbers represent like elements in the figures. The activity sensor 36 incorporates an extension 40 which mounts the mass 42 at a small distance from the surface of the piezoelectric film 24. The extension 40 is mounted via a foot 44 affixed to one of the major surfaces of the piezoelectric film 24, or the metallized surface 26.

Figure 3:
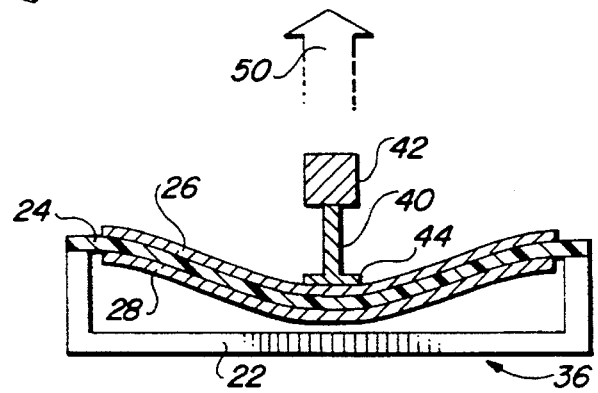
FIG. 3 is a side view of the activity sensor of FIG. 2 undergoing a vertical acceleration.
Figure 4:
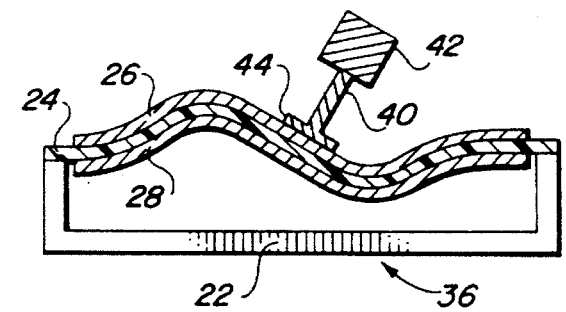
FIG. 4 is a side view of the activity sensor of FIG. 2 undergoing a horizontal acceleration.

Cantilevering the mass 42 provides an increased sensitivity for the activity sensor 36. FIGS. 3 through 4 illustrate the activity sensor 36 under the influence of acceleration forces directed along the three axes. It should be understood that an acceleration applied to the activity sensor 36 at any angle could be analyzed as a vector combination of two or more of the accelerations illustrated in FIGS. 3 through 5.

In FIG. 3, an acceleration directed upward along the vertical axis as shown by arrow 50 as applied to the activity sensor 36. This upward acceleration is resisted by the inertia of the mass 42, causing the film 24 to flex, thereby placing the piezoelectric film 24 in stress and producing an output signal on conductors 30 and 32.

In FIG. 4, a horizontal acceleration represented by arrow 52 is applied to the activity sensor 36. Again this acceleration is resisted by the inertia of the mass 42, causing a rotation of the cantilevered mass 42, twisting and stretching the film 24 resulting in an output signal on conductors 30 and 32.

Figure 5:
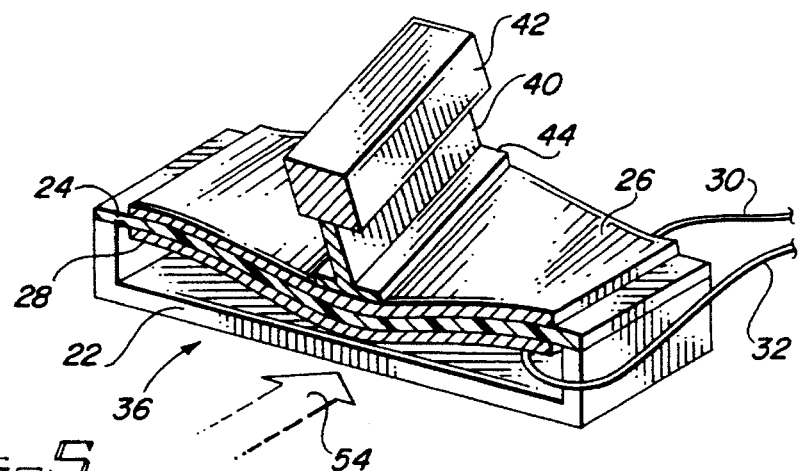
FIG. 5 depicts an isometric view of the activity sensor of FIG. 2 under the influence of an acceleration transverse to the plane of the sensor.

FIG. 5 depicts an acceleration transverse to the plane of the film 36, as shown by arrow 54, applied to the activity sensor 40. The transverse acceleration causes a rotational acceleration of the cantilevered mass 42. This rotational acceleration of the cantilevered mass 42 will cause a twisting of the film 24. The twisting within the film 24 will produce an output signal which is in proportion to the change in applied inertial and/or gravitational forces.

It should be understood that the acceleration forces illustrated in FIGS. 3 through 5 will not be continuous, and that usually after a brief acceleration there will be a reversal or a deceleration. However, once accelerated, the mass 42 will resist the deceleration producing flexure opposite that shown in FIGS. 3 through 5. As a result, the activity sensor 36 will oscillate, until resistance causes attenuation, producing a time varying signal output on conductors 30 and 32. This time varying output will be a functional characteristic of the magnitude and direction of the applied acceleration, as well as the inherent characteristics of the activity sensor 36. Further, the output signal can be different for each of the three axes and can be controlled by sizing and placement of the mass 42, as well as by controlling the width, length and thickness of the piezoelectric film 24.

Because of the sagittal multiplication of forces, the embodiments of FIGS. 1 and 2 will be very sensitive to the changes of acceleration normal to the plane of the thin film 24. By cantilevering the mass and tailoring the dimensions of the thin film 24, extension 42, and the foot 44 for the mass 42 depicted in FIG. 2, the sensitivity can be increased selectively in the horizontal and transverse axes.

The embodiments of FIGS. 1 and 2 may be designed to have a length for the film 24 which is greater than the distance between the spacing of the locations of attachment to the frame assembly 22. Thereby, the piezoelectric film 24 may be slack during assembly, so that the weight of the mass 34 or 42 will cause a sagging of the film 24. This design will provide a signal output which will include a series of pulses when the mass shifts, thereby suddenly taking up the slack and suddenly inducing stress in the film 24. The output signals will be the absolute value of a changing acceleration for a taut piezoelectric film version and a series of unipolar pulses for a slack piezoelectric film version of the activity sensors 20 or 36.

FIGS. 6 and 7 depict a cube-shaped activity sensor 60 in the assembled and unassembled configuration, respectively. The cubed-shaped activity sensor 60 of FIGS. 6 and 7 includes six sides: 62, 64, 66, 68, 70 and 72 which when assembled, form a hollow box. For example, each of the sides 62–72 can be formed from a single piezoelectric sheet 74 which can be cut to the cross shape shown in FIG. 7, creased at the edges adjoining respective sides, and then sandwiched between an inner and an outer conductive metallic coating, 80 and 82 respectively. The remaining peripheral edges of the six sides 62, 64, 66, 68, 70 and 72 are interconnected during assembly, for example by gluing.

As illustrated, in FIG. 7, the respective conductive metallic coating 80 on the inner surfaces of the sides 62–72 may be interconnected with jumper wires 84 to provide a single output from the internally located metallic coatings 80. As an alternative, the conductive metallic coating 80 and 82 may be formed as one continuous sheet so as to form one single continuous conductor over a plurality of, and preferably all the edges 62–72. Furthermore, the single continuous sheet may be formed on each of the major surfaces. Accordingly, only one electrical conductor is electrically coupled to each sheet to provide respective electrical outputs from each sheet. A hole through one of the sides, e.g. side 66, provides an outlet for a conductor 86 carrying the signal. In addition, the conductive metallic coatings 82 on the outside of each of the respective sides 62–72 may be interconnected via jumper wires 88 to ultimately provide a single output at conductor 90. Alternatively, each of the metallic coatings 80 and 82 for the respective sides 62–72 may have its own output conductors.

A spherical mass 92 is encased within the activity sensor 60 during assembly as shown in FIG. 6. The presence of the spherical mass 92 provides a mass element which will exert a reactive force against the respective sides 62–72, in response to specific motions or accelerations. It should be noted that by tipping the activity sensor 66 on one corner, the spherical mass 92 will normally be at rest against three of the six sides. Vertical acceleration will cause the spherical mass 92 to exert forces on the respective three sides, and, when the acceleration is reversed, the spherical mass 92 will move upward and contact at least one of the opposite three sides, providing an output signal therefrom.

FIGS. 8 and 9 depict an alternative view of a tetrahedron shaped activity sensor 100 having four sides 102, 104, 106, 108 each of which is formed from a piezoelectric film 110, creased and then sandwiched between an internal and external conductive metallic layer 112 and 114, respectively. Similarly, and as priorly discussed, the conductive metallic coatings 112 and 114 may be formed as one continuous sheet. As in the embodiment of FIGS. 6 and 7, the tetrahedral configuration includes an enclosed spherical mass 120 contained within the tetrahedron. Electrical signals are taken via output conductors 122 and 124 from the internal and external conductive layers 112, 114. In addition, the internal conductive layers 112 may be interconnected via jumper wires 126, and the external conductive layers 114 may also be interconnected via wires 128.

In either of the configurations, according to FIGS. 6–7 or 8–9, the mass 92 and 120 may be sized to be significantly smaller than the internal dimensions of the enclosure, or it may be sized to fit snugly within the enclosure. If the mass 92, 120 is smaller than the internal dimensions of the enclosure. Preferably, the mass will be free to move in response to motion and acceleration. However, if the mass is sized to fit snugly within the enclosure, then any acceleration or motion will cause a direct output on at least one of the surfaces, and usually an output against at least two surface. As in the embodiments for FIGS. 6 and 7, the embodiment of FIG. 8 and 9 may be turned to have the mass 120 normally positioned against three of the respective triangular surfaces during any upright physical activity. In this manner, the spherical mass 120 can exert a force against the respective three walls of the tetrahedron shaped activity sensor 100, and variations in the forces exerted on the walls produce output signals for monitoring physical activity.

Figure 10:
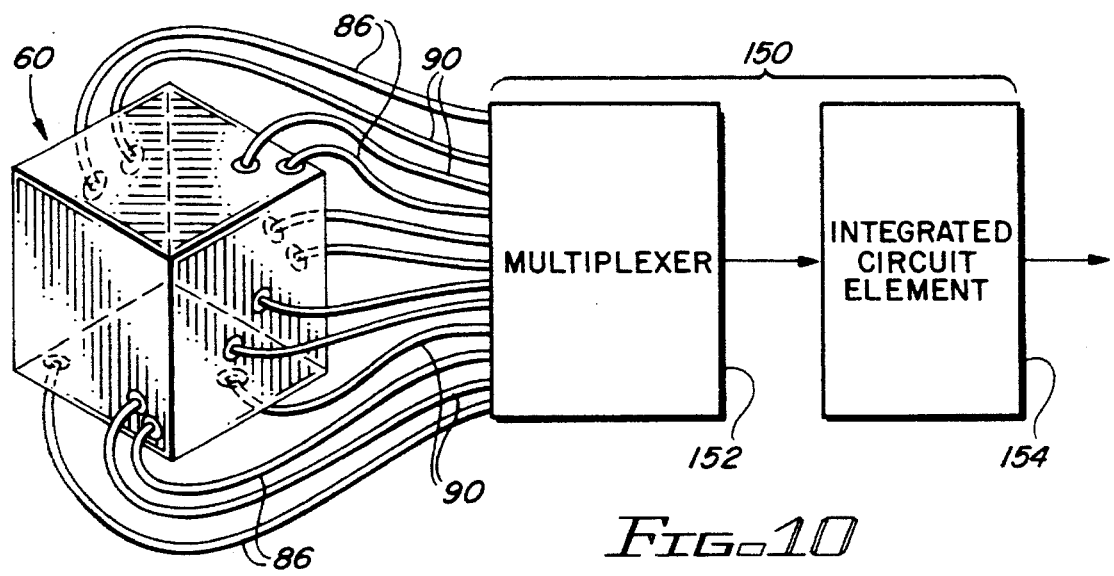
FIG. 10 depicts a simple block diagram of a portion of the signal processing circuit within the pacemaker, attached to the cube shaped activity sensor of FIG. 6.

Each of the foregoing activity sensors must be interconnected to the logic, timing and pulse generating circuitry of the pacemaker 16, to provide an electrical signal which can be used to derive the patient's activity level. A basic block diagram of the cube shaped activity sensor 60 of FIGS. 6 and 7 interconnected to a signal processing circuit 150 is illustrated in FIG. 10. It should be appreciated that the signal processing circuit 150 depicted in FIG. 10 could also be used with the other activity sensor embodiments disclosed herein.

The signal processing circuit 150 may include a multiplexer 152 for receiving the signals from the various conductors 86 and 90 attached to the respective metallic coatings on the inside and outside of the cube shaped activity sensor 60. As compared to the embodiments of FIGS. 6–7, the activity sensor 60 of FIG. 10 includes a plurality of individual conductors 86 and 90 connected to the inside and outside metallic coatings 82, 80 respectively, to bring signals from each side of the cube shaped activity sensor 60 to the multiplexer 152.

The signal processing circuit 150 may also include an integrated circuit element 154 for processing the respective signals. The integrated circuit element 154 can include a variety of logic programs for utilizing the signal information produced by the cube shaped activity sensor 60, depending on the specific requirements and configuration of the activity sensor 60.

It should be evident from the foregoing that the present invention provides many advantages over activity sensors for implanted medical devices of the prior art. Although preferred embodiments are specifically illustrated herein, it will be appreciated that many modifications and variations of the present invention are possible in light of the above teachings to those skilled in the art. It is therefore to be understood that the present invention is limited only by the proper literal and equivalent scope of the appended claims.

What is claimed is:

1. An implantable medical device for monitoring physical activity of a patient, comprising:

a housing assembly suitable for implantation in body tissue;

a frame assembly mounted within said housing assembly;

a piezoelectric film having opposing major surfaces and respective ends attached to said frame assembly so that said piezoelectric film is supported within said frame assembly;

a pair of conductive metal coatings affixed to opposite major surfaces of said piezoelectric film;

a pair of electrical conductors, each attached to one of said pair of conductive metal coatings; and a mass element operative with said piezoelectric film to increase stress applied to said piezoelectric film as a result of acceleration of the of the patient.

2. The implantable medical device of claim 1, wherein said mass element is affixed to one of said major surfaces of said piezoelectric film.

3. The implantable medical device of claim 1, further comprising:

a cantilever element having a first end affixed to one of said major surfaces of said piezoelectric film and a second end attached to said mass element to space said mass element from said piezoelectric film.

4. The implantable medical device of claim 1, wherein said piezoelectric film is a thin film of polyvinylidene fluoride.

5. The implantable medical device of claim 1, wherein:

said frame assembly has a predetermined length; and said piezoelectric film has a length slightly greater than said predetermined length of said frame assembly.

6. The implantable medical device of claim 5, further comprising:

a cantilever element having a first end affixed to one of said major surfaces of said piezoelectric film and a second end attached to said mass element to space said mass element from said piezoelectric film.

7. An implantable medical device for monitoring physical activity of a patient, comprising:

a housing assembly suitable for implantation in body tissue:

a piezoelectric film having opposite major surfaces with metallic coatings affixed thereto, said piezoelectric film having a first predetermined length, the piezoelectric film having a first end and a second end opposite the first end;

means for supporting said piezoelectric film within said housing assembly by the first and second ends, said supporting means having a second predetermined length slightly less than said first predetermined length of said piezoelectric film so that the piezoelectric film is slightly slack;

conductor means for interconnecting said metallic coatings and said electrical circuitry in said housing assembly; and mass means operative with said piezoelectric film for increasing stress in said piezoelectric film as a result of acceleration of the of the patient, whereby the mass causes the piezoelectric film to sag.

8. An implantable stimulation device, comprising:

pulse generating means for generating stimulation pulses to the heart at a variable rate;

activity sensing means for sensing physical activity of a patient, said activity sensing means including:

a frame assembly mounted within said housing assembly;

a piezoelectric film having opposing major surfaces and respective ends attached to said frame assembly so that said piezoelectric film is supported within said frame assembly;

a pair of conductive metal coatings affixed to opposite major surfaces of said piezoelectric film;

a pair of electrical conductors, each attached to one of said pair of conductive metal coatings; and a mass element operative with said piezoelectric film to increase stress applied to said piezoelectric film as a result of acceleration of the patient;

processing means for determining said variable rate of stimulation pulses based on said activity sensing means; and a housing assembly, suitable for implantation in body tissue, for housing said pulse generating means, said activity sensing means and said processing means.

9. The implantable stimulation device of claim 8, wherein said mass element is affixed to one of said major surfaces of said piezoelectric film.

10. The implantable stimulation device of claim 8, wherein said activity sensing means further comprises:

a cantilever element having a first end affixed to one of said major surfaces of said piezoelectric film and a second end attached to said mass element to space said mass element from said piezoelectric film.

11. The implantable stimulation device of claim 8, wherein said piezoelectric film is a thin film of polyvinylidene fluoride.

12. The implantable stimulation device of claim 8, wherein:

said frame assembly has a predetermined length; and said piezoelectric film has a length slightly greater than said predetermined length of said frame assembly.

13. The implantable stimulation device of claim 12, wherein said activity sensing means further comprises:

a cantilever element having a first end affixed to one of said major surfaces of said piezoelectric film and a second end attached to said mass element to space said mass element from said piezoelectric film.

* * * * *